United States Patent [19]
Kricka

[11] Patent Number: 5,302,533
[45] Date of Patent: Apr. 12, 1994

[54] ANTIBODY-ENHANCED CHEMILUMINESCENCE REACTIONS

[75] Inventor: Larry J. Kricka, Berwyn, Pa.

[73] Assignee: British Technology Group Limited, London, England

[21] Appl. No.: 866,043

[22] Filed: Apr. 10, 1992

[51] Int. Cl.$^5$ ............... G01N 33/542; G01N 33/563; C07K 15/06
[52] U.S. Cl. .................................. 436/537; 436/513; 435/188.5; 435/968; 530/388.9; 530/389.8
[58] Field of Search ............... 436/513, 537; 435/183, 435/188.5, 968; 530/388.9, 389.8

[56] References Cited

U.S. PATENT DOCUMENTS

| | | | |
|---|---|---|---|
| 4,792,446 | 12/1988 | Kim et al. | 424/85.8 |
| 4,888,281 | 12/1989 | Schochetman et al. | 435/72 |
| 4,963,355 | 10/1990 | Kim et al. | 424/85.8 |
| 5,037,750 | 8/1991 | Schochetman et al. | 435/183 |

OTHER PUBLICATIONS

Shultz et al. C&EN, May 28, 1990.
Kricka et al.; Chapter 6, pp. 77–98, from handbook by CRC, Luminescence Immunoassay, CRC Press, 1990.
Brundett et al.; "Yields of Chemically Excited States" J. Am Chem Soc; 94:21, Oct. 18, 1972, pp. 7536–7541.
Kohen et al; "An assay for urinary estriol &-glucuronide–" Steriods; vol. 36(4), Oct. 1980 pp. 405–419.

Primary Examiner—Christine M. Nucker
Assistant Examiner—M. P. Woodward
Attorney, Agent, or Firm—Nixon & Vanderhye

[57] ABSTRACT

A method of increasing the light output from a chemiluminescent reaction of a dihydrophthalazinedione (DPD), and an oxidant, which comprises carrying out said reaction in the presence of at least one antibody, raised against an intermediate species of said chemiluminescent reaction.

15 Claims, 2 Drawing Sheets

ANTIBODY-ENHANCED CHEMILUMINESCENCE REACTIONS

BACKGROUND OF THE INVENTION

1. Field of the Invention

The present invention relates to an enhanced chemiluminescent reaction especially for use in a diagnostic assay, particularly immunoassay, and to a diagnostic kit for use in the assay. A chemiluminescent reaction is a chemical reaction which results in the emission of light. The luminescent emission is generally of sufficient duration to enable the light emitted to be detected or measured, and thereby to allow the detection or quantification of an analyte. The chemiluminescent reaction with which this invention is concerned is that between a 2,3-dihydro-1,4-phthalazinedione (DPD), especially luminol, with an oxidant, especially hydrogen peroxide, and a peroxidase enzyme, especially horseradish peroxidase, which catalyses the oxidation of the DPD by the oxidant. The oxidation is accompanied by emission of light.

2. Description of the Prior Art

Luminescent assays making use of the above-mentioned peroxidase-catalysed oxidation of a DPD include several types. It includes predominantly assays wherein horseradish peroxidase is conjugated to a ligand in order to label it and a luminescent reaction is used to detect or quantitate the label. This category includes ELISAs, competitive EIAs and nucleic acid hybridization assays, based on peroxidase labels. However, assays for measurement of free peroxidase, e.g. for analytical purposes, are also included.

A review of luminescent assays has been published by L. J. Kricka, Clinical Chemistry 37, 1472–1481 (1991).

The sensitivity of the peroxidase-catalysed chemiluminescent oxidation of DPDs can be enhanced by including an enhancer in the reaction. Such enhancers include a 6-hydroxybenzothiazole (European Patent 87959B), a phenol selected from a narrowly defined class (U.S. Pat. No. 4,598,044), an aromatic amine selected from a narrowly defined class (U.S. Pat. No. 4,729,950) or phenols substituted in ortho and/or para positions by imidazole or benzimidazole (European Patent 296752B), all owned by National Research Development Corporation. A further number of aromatic amine enhancers are disclosed in European Patent Application No. 219352A (Minnesota Mining & Manufacturing Co).

The present invention involves a new approach to increasing light output from chemiluminescent reactions and therefore further prior art will be discussed below after the "Summary of Invention" where it can be understood in context.

SUMMARY OF THE INVENTION

An object of the invention is to provide a method of increasing the light output from a chemiluminescent reaction of a dihydrophthalazinedione (DPD) and an oxidant, which comprises carrying out said reaction in the presence of an antibody raised against an intermediate species of said chemiluminescent reaction. These antibodies are hereinafter referred to as "catalytic antibodies".

The term "intermediate species" is herein used to include any of the transient intermediary compounds formed in the oxidation of the DPD during the chemiluminescent reaction.

Preferably, said antibody is polyclonal or more preferably monoclonal.

While the invention applies to increasing the light output from any chemiluminescent reaction involving the above-stated reaction partners, for any purpose, it is primarily of interest in connection with an assay. The term "assay" herein covers detection, semi-quantitation and quantitation. Typically, the assay is carried out so that the light output is relatable to the amount of catalytic antibody or luminol employed, the catalytic antibody or luminol then being the substance directly determined.

Although the invention is usable to determine the presence or amount of any one of the three above-stated reaction partners, such a reaction partner is not necessarily itself the substance to be assayed. Thus, the oxidant can be produced as a result of an earlier reaction or cascade of earlier reactions carried out on a sample. The catalytic antibody or the luminol can be in the form of a conjugate to, say, an antibody which is used in an immunoassay to determine an antigen. The invention is accordingly applicable to any method of diagnostic assay of a substance, the presence or amount of which is relatable to the presence or amount of a reaction partner selected from the group consisting of a DPD, a said catalytic antibody and an oxidant which together are reactable in a chemiluminescent reaction and wherein the reaction is carried out, the light output is detected or measured and thence the presence or amount of the substance to be assayed is related to the light output.

The invention also includes a kit for use in the assay comprising the DPD, and an antibody of the invention. The oxidant could be supplied separately or included in the kit. The invention further includes the antibodies raised against an intermediate species of said chemiluminescent reaction, and fragments of those antibodies.

DESCRIPTION OF FURTHER PRIOR ART

There have recently been several attempts to utilise antibodies to increase the rate of chemical reactions. Such antibodies have been described as catalytic antibodies or abzymes. A thorough background on this topic can be found in K. M. Shokat and P. G. Shultz Annual Review Immunology (1990) 8 355–363. The authors review the application of catalytic antibody techniques to catalyzing a range of chemical reactions including ester and amide bond hydrolysis, concerted Claisen rearrangements, elimination reactions, photochemical thymine dimer cleavage, redox reactions, lactonization reactions and bimolecular amine bond formation.

More recently, U.S. Pat. No. 4,888,281 (Igen Inc.) discloses the use of monoclonal antibodies to increase the rate of a number of chemical reactions including enzyme-catalysed reactions.

There has been no suggestion in the literature that antibodies could be used to improve the sensitivity of chemiluminescent reactions.

DESCRIPTION OF THE PREFERRED EMBODIMENTS

Figure 1:
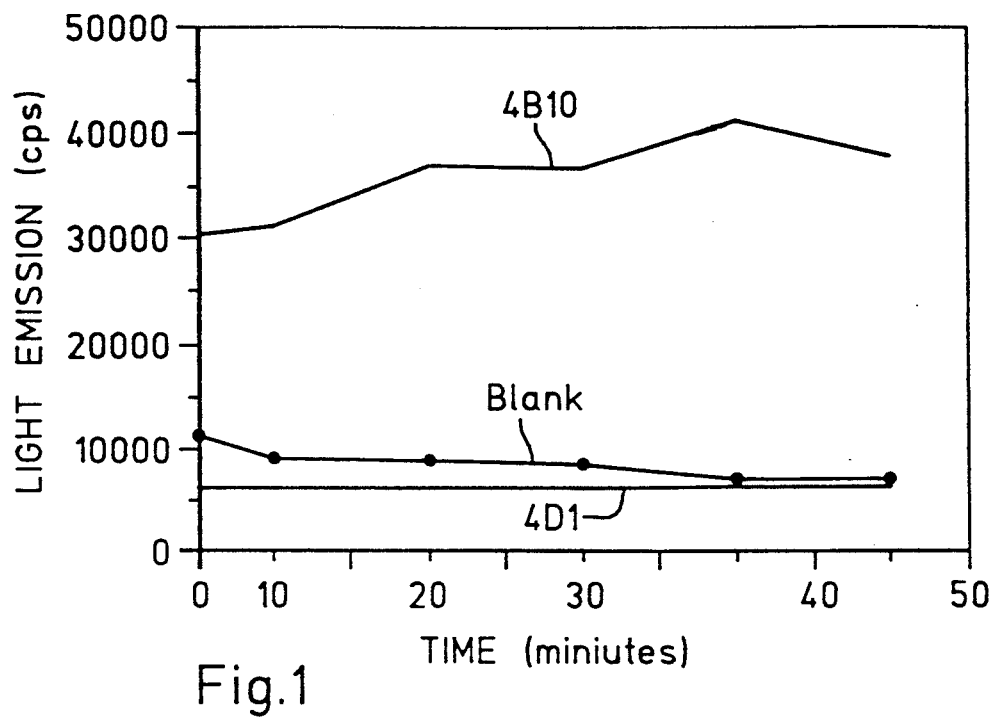
FIGS. 1–4 show the light emission from antibodies isolated at various points in the purification process 4B10 is an antibody raised against a chemiluminescent reaction intermediate and A, B and C relate to dilutions of 4B10, whereas 4D1 is a different antibody isolated during the preparation of 4B10 that does not enhance chemiluminescence.

As indicated above, the present invention provides a method for increasing the light output of DPD/oxidant chemiluminescent reactions. The method involves performing the reaction in the presence of an antibody, preferably a monoclonal antibody, that is specific for a reaction intermediate.

Such monoclonal antibodies may be prepared by methods well known in the art. Typically this initially involves immunizing mice or other suitable mammals with an appropriate chemiluminescent reaction intermediate as the antigen. An appropriate antigen in the chemiluminscent reaction involving luminol and hydrogen peroxide is 3-aminophthalic acid (APA) or molecules with a 3-aminophthalic acid moiety.

For immunizing mice, the antigen is conveniently coupled to a carrier molecule such a bovine serum albumin (BSA) or keyhole limpet hemocyanin (KLH). Antibody-producing lymphocytes are then removed from the spleens of the immunized mice and hybridized to myeloma cells such as SP2/0 cells to produce hybridoma cells. These hybridoma cells are then plated in the wells of microtiter plates. The series of monocolonal antibodies produced is screened under appropriate conditions to identify monoclonal antibodies that increase the high output of the chemiluminescent reaction.

The clone producing the desired catalytic antibody may then be cultured to yield colonies which may in turn be propagated in vitro or in vivo.

In normal practice of the invention, the antibody is added to the chemiluminescent reactants prior to the initiation of the reaction.

The best results are obtained at around neutral pH. Preferably the pH is in the range 6 to 8 at the time of mixing all the reagents.

Any chemiluminescent DPD can be used in the invention, that is to say any DPD which is oxidisable by an added oxidant to give chemiluminescence can be used. Examples are luminol, isoluminol, 4-[N-(4-aminobutyl)-N-ethylamino]isoluminol (ABEI), and 7 -dimethylaminonaphthalene-1, 2-dicarboxylic acid hydrazide, of which luminol is normally preferred. The DPD can be free or conjugated to a ligand to provide a direct label. Such luminophore-labelled assays are known in the art. The DPD chosen will ultimately determine which reaction intermediate is chosen for antibody generation e.g. 3-amino-phthalic acid for luminol, 4-amino-phthalic acid for isoluminol or aminobutyl-ethylamino-phthalic acid for ABEI.

The oxidant can be any added substance (not oxygen itself) which oxidises the DPD in a light-emitting reaction; hydrogen peroxide is usual, but a perborate, such as the sodium salt, is an alternative.

The concentrations of the reaction partners of the chemiluminescent reaction will depend on the nature of the assay being carried out and particularly on which of them is being assayed. Generally stated, the light output is greater, the greater the concentration of DPD. Thus, when the antibody or oxidant is being assayed, the use of excess DPD is recommended. Generally stated, the DPD concentration is desirably from 0.5 micromole to 200 millimoles per liter, preferably 0.5 to 100 micromoles/liter. Generally stated, the oxidant concentration is desirably in the range 0.5 micromoles to 300 millimoles/liter, preferably 10 to 200 millimoles/liter.

The catalytic antibodies of the present invention will also be of use in those situations where a high degree of sensitivity is required, for example, blotting assays, including Western, Southern and Northern blotting assays, as well as dot blots and other nucleic acid hybridisation assays.

A further potential use of the catalytic antibodies is in non-separation immunoassay formats in conjunction with a luminol label. For example, binding of a luminol labeled drug to a specific drug antibody would prevent interaction between the luminol label and added catalytic antibody. However, in the presence of the drug, relatively less luminol labeled drug would be bound to the drug antibody, and the luminol label would interact effectively with the catalytic antibody. The degree of modulation of the light emission would give an indication of drug concentration.

Another further use for the catalytic antibodies described above is in enhanced-peroxidase/DPD/oxidant chemiluminescent reactions where it is believed that the catalytic antibody will further increase the light output.

EXAMPLE

Preparation of a Catalytic Antibody Capable of Increasing Light Output from a Chemiluminescent Reaction

1. Materials and Methods

Luminol (Aldrich, Milwaukee, Wis.) was purified by recrystallization from sodium hydroxide as described previously (Ham G. et al. Anal. Lett.12, 535–541, 1979).

Immunogens

APA (Kodak, Rochester, N.Y.) was conjugated to keyhole limpet hemocyanin (KLH) and bovine serum albumin (BSA) using a Pierce Imject Immunogen EDC conjugation kit with BSA and KLH (Pierce, Rockford, Ill.) following the manufacturers' instructions.

Monoclonal Antibodies

Monoclonal antibodies were produced by BAbCO (Richmond, Calif. 94806) following standard protocols. An ELISA (immobilized APA-KLH or APA-BSA capture antigen) was used to screen ascites fluid for the presence of monoclonal antibodies with the required specificity.

Chemiluminescence Screening Procedure

A luminol-hydrogen peroxide reagent was prepared as follows: sodium luminol (12.5 mg) was dissolved in 50 ml of Tris buffer (0.1 mol/l, pH 7.2), and 15.5 $\mu$l of hydrogen peroxide (Sigma, 30% w/v) was mixed with 0.5 ml of Tris buffer (0.1 mol/l, pH 7.2). These two solutions were combined and protected from light. The luminol-hydrogen peroxide reagent (100 $\mu$l) and the test sample (2–10 $\mu$l) were mixed in an assay tube, and the light emission was measured using either a Berthold Biolumat LB9500C (Nashua, N.H.) or a Dynatech ML1000 microplate luminometer. Assays were also performed using 1:10 and 1:50 dilutions of the luminol-peroxide reagent in the pH 7.2 Tris buffer.

High Resolution Electrophoresis and Immunofixation

High-resolution agarose gel electrophoresis (Helena Laboratories, Beaumont, Tex.) was performed following the manufacturer's protocol. Anti-mouse IgG (gamma-chain specific) and IgM (μ-chain specific) antisera for immunofixation were purchased from Sigma and anti-kappa and anti-lambda light chain antisera were from Atlantic Antibodies (Stillwater, Minn.).

2. Isolation and Purification of Clones and Antibodies

I Purification of Antibody by Ammonium Sulfate Precipitation

A saturated ammonium sulfate solution was prepared by dissolving 152.2 g ammonium sulfate in 200 ml distilled water. The mouse ascites fluid referred to above was centrifuged at 3000 g for 30 minutes and the supernatant transferred to a beaker. Saturated ammonium sulfate (equal to 50% of volume of supernatant) was added slowly with stirring to the supernatant. The mixture was stored overnight at 4° C. and then centrifuged at 3000 g for 30 minutes. The supernatant was removed and saturated ammonium sulfate solution (equal to 50% of volume of the original supernatant) was added slowly with stirring. The mixture was stored overnight at 4° C. The precipitate was harvested by centrifugation (3000 g, 30 minutes) and resuspended in 0.3–0.5 of starting volume of PBS (pH 7.2) and dialyzed in PBS overnight.

II Purification of the Antibody Using DEAE-Affi-gel Blue Chromatography

A sample of antibody purified by ammonium sulfate precipitation (100 μl) was dialyzed in column buffer (20 mM Tris buffer containing 25 mM sodium chloride, pH 7.2) overnight at 4° C. This sample was applied to a column (K9/15) of DEAE-Affi-gel blue (10 ml) and the column was washed with 3 bed volumes of 25 mmol/l sodium chloride and eluted with 3 bed volumes of 20 mmol/l Tris buffer (pH 7.2) containing 50 mmol/l sodium chloride. The column fractions were tested using the chemiluminescence assay described previously. The protein concentration of selected fractions was measured using the Bio-Rad (Richmond, Calif.) protein assay. The fractions #3–#6 were then concentrated (25-fold) by dialysis, using a Minicon-B15 (Amicon, Denvers, Mass.).

III Purification of the Antibody Using Gel-filtration (G-200) Chromatography

A 100 μl sample of the antibody purified by ammonium sulfate precipitation was chromatographed on a column (2 ml) of Sephadex G-200 (Sigma). The column was eluted with PBS (15 ml) and the fractions tested using the chemiluminescence assay described previously. Fractions #6–#9 were concentrated by evaporation in vacuo, using a Speed Vac (Savant Instruments, Farmingdale, N.Y.) and retested.

IV Purification of the Antibody by Affinity Chromatography Using Immobilized Antimouse IgM (μ Chain Specific)

A column was prepared containing 2 g (1 ml) of agarose-anti-mouse IgM (μ chain specific)(Sigma). It was washed succesively with 10 bed volumes of Tris buffer (10 mmol/l, pH 7.5), glycine buffer (100 mmol/l, pH 2.5), Tris buffer (10 mmol/l, pH 8.8), triethylamine (100 mmol/l, pH 11.5) and finally, Tris buffer (10 mmol/l, pH 7.5). A sample (100 μl) of the antibody (from clone 4B10) was purified by ammonium sulfate precipitation from ascites fluid was applied to the column. The column was then washed with 10 bed volumes of the pH 7.5 Tris buffer. Bound antibody (acid sensitive) was eluted with 10 bed volumes of the pH 2.5 glycine buffer. The column was then washed with 10 bed volumes of the pH 8.8 Tris buffer. Any remaining bound antibody (base sensitive) was eluted with the pH 11.5 triethylamine buffer. The fractions were then tested for chemiluminescent activity, dialyzed against PBS, lyophilized, reconstituted with 100 μl distilled water and retested, and finally then redialyzed and retested. The various fractions and concentrated fractions were also analyzed by agarose gel electrophoresis.

Va Preparation of Sepharose-APA Affinity Chromatography Medium

Cyanogen bromide-activated Sepharose 4B (1 g, Sigma) was washed with 200 μl of cold distilled water, and then centrifuged at 3000 rpm for 5 minutes. The supernatant was removed and the gel rewashed with 200 μl of cold sodium pyrophosphate buffer (0.1 mol/l, pH 8.0). The washed gel was suspended in a solution of APA (5 ml, 1 mg/ml in 0.1 mol/l sodium pyrophosphate buffer, pH 8.0) and the mixture stirred overnight at 4° C. The gel was then washed with 200 ml of cold distilled water and sodium pyrophosphate buffer (0.1 mol/l, pH 8.0) and then suspended in sodium pyrophosphate buffer (0.1 mol/l, pH 8.0) and stored at 4° C.

Vb Purification of Antibody by Affinity Chromatography Using Sepharose-APA

A column was prepared containing 1 ml of Sepharose-APA. It was washed succesively with 10 bed volumes of Tris buffer (10 mmol/l, pH 7.5), glycine buffer (100 mmol/l, pH 2.5), Tris buffer (10 mmol/l, pH 8.8), triethylamine (100 mmol/l, pH 11.5) and finally, Tris buffer (10 mmol/l, pH 7.5). A sample (100 μl) of the antibody (from clone 4B10) purified by ammonium sulfate precipitation from ascites fluid was applied to the column. The column was then washed with 10 bed volumes of the pH 7.5 Tris buffer. Bound antibody (acid sensitive) was eluted with 10 bed volumes of the pH 2.5 glycine buffer. The column was then washed with 10 bed volumes of the pH 8.8 Tris buffer. Any remaining bound antibody (base sensitive) was eluted with the pH 11.5 triethylamine buffer. The fractions were then tested for chemiluminescent activity, dialyzed against PBS, lyophilized, reconstituted with 100 μl distilled water and retested, and finally the redialyzed and retested. The various fractions and concentrated fractions were also analyzed by high-resolution agarose gel electrophoresis.

A sample (30 μl) of the antibody purified by ammonium sulfate precipitation from ascites fluid (4B10-D1) was incubated with 20 mg Sepharose-APA for 15 minutes at room temperature. The mixture was centrifuged and a sample of the supernatant and the Sepharose-APA (after washing with the Tris buffer) was tested using the chemiluminescence assay.

VI Purification of Antibody by Excision From Agarose Electrophoresis Gel

Multiple samples (2 μl) of the ascites fluid were electrophoresed on agarose gel. One lane was removed and stained for protein so as to provide the location of the bands. Areas of gel corresponding to the principal bands were removed and triturated with the pH 7.2 Tris buffer. The extracts were tested for catalytic activity in the luminol reaction as described previously.

VII Heat Inactivation of Purified Antibody

A sample of antibody (4B10, 2 μl) purified by ammonium sulfate precipitation was heated at 95° C. for 10 minutes and then cooled in an ice bath. The antibody was tested before and after heating using the chemiluminescence assay described previously.

VIII Testing of Irrelevant Mouse IgMs

An IgM kappa (TEPC18) and an IgM lambda (MOPC 104E) monoclonal antibody (Sigma) were dissolved in pH 7.2 Tris and tested for activity in the luminol-peroxide reaction as described previously.

RESULTS

The luminol-peroxide chemiluminescent reaction was used to test the various antibody preparations. This reaction was performed at pH 7.2 in order to favor reaction with the antibody, and to minimize catalysis by any metal ion or peroxidase contaminants.

Selection of Clones

The different antisera were ranked according to maximum light emission intensity in the chemiluminescent and ELISA screening tests. Based on this data two antisera were selected from the APA-BSA immunizations and from the APA-KLH immunizations. In both cases the light emission was significantly greater than the control. The various fusions were screened and seven clones were selected for ascites fluid production.

Ammonium sulfate purified preparations of ascites fluid (section 2 step I) from three of the clones (4A4, 4B10, 4F8) all produced a significant increase in light emission compared to the luminol-peroxide control. The most active antibody was from clone 4B10 and this increased the light emission more than 3 times greater than the control at 30 minutes after initiation of the luminescent reaction (FIG. 1). In contrast, antibodies from the clone 4D1 caused a decrease in light emission under identical conditions and were therefore discarded. The 4B10 clone was selected for further detailed study.

Characterization of 4B10

The antibody was characterized as an IgM lambda and the ammonium sulfate-purified antibody was unstable to long term storage (6 months, 4° C.). Heat treatment of the purified antibody abolished its activity in the luminol-peroxide reaction. Purification of the antibody was investigated using a range of chromatographic and electrophoretic techniques.

Purification by Excision From an Agarose Electrophoresis Gel

Electrophoresis showed the presence of two bands (bands 1 and 2) in the gamma region and one band (band 3) in the alpha region. The principal IgM band (band 1) and a second band which did not react with anti-IgG, IgA, IgM, kappa or lambda (band 2) both showed considerable chemiluminescent activity compared to the albumin band (band 3) which served as a control. The albumin band quenched the light emission from the luminol-peroxide reaction and this effect of proteins has been described previously [(Schroeder H. R. et al., Methods Enzymol. 57 424–445 (1978)].

DEAE-Affi-gel Chromatography (Section 2 Step II)

Figure 2:
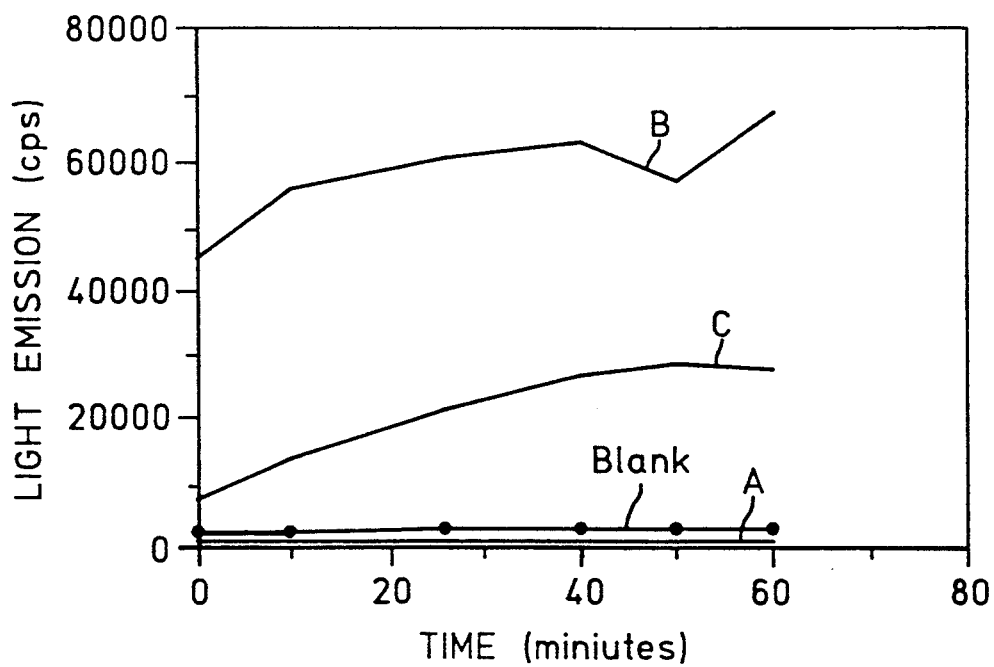

A series of highly active fractions were obtained by ion-exchange chromatography. The purified antibody from clone 4B10 (1.5 mg/ml) produced a dose-dependent increase in light emission in the luminol-peroxide reaction (FIG. 2). FIG. 2 shows the effect of A, 2 μl of a 1:100 dilution of antibody, B, 2 μl of a 1:2 dilution and C 10 μl undiluted sample of 4B10 antibodies. The antibody proved unstable and lost all activity after a relatively short period of storage (48 hours, 4° C.).

Gel Filtration Chromatography (Section 2 Step III)

The high molecular weight fractions had the highest chemiluminescent activity and these were concentrated and retested. The concentrated fractions still showed activity 3-times greater than the luminol-peroxide control value.

Affinity Chromatography Using Immobilized Anti-mouse IgM (u) (Section 2 Step IV)

Figure 3:
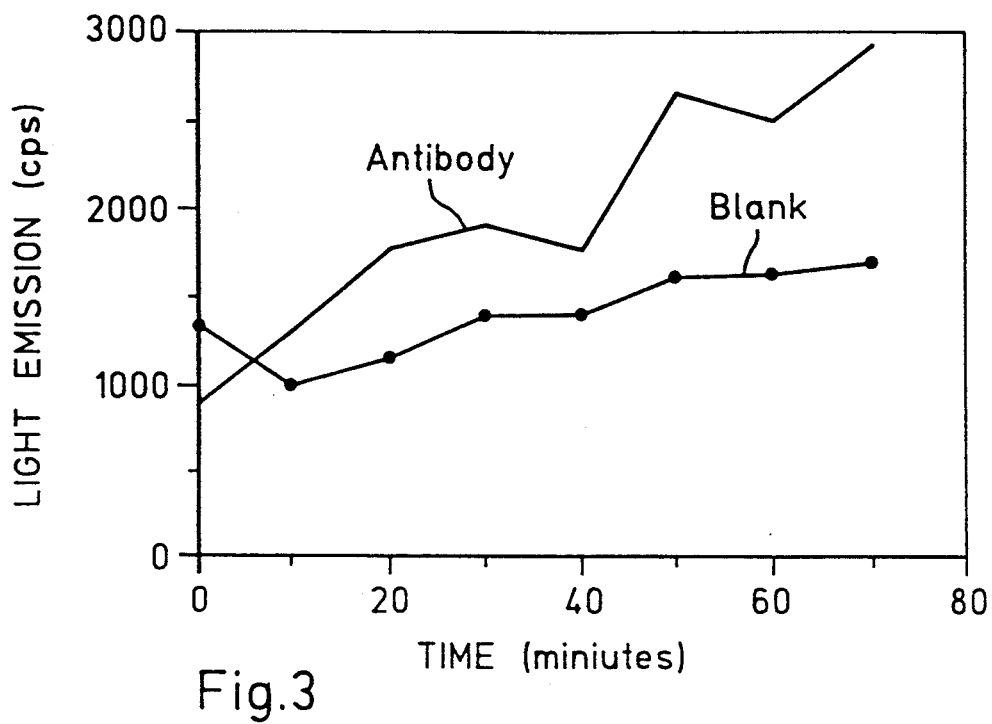

The antibody was purified using an immobilized antibody that recognized mouse IgM heavy chain. The acidic elution procedure eluted a material which showed activity approximately 2-fold greater than the blank after it had been concentrated by lyophilization (FIG. 3). The various fractions were also analyzed by agarose gel electrophoresis. The acid eluate showed the presence of the IgM monoclonal antibody (band 1) and albumin (band 3). The other band (band 2) that migrated in the fast gamma region did not bind to the column and was found in fraction A. After concentration, agarose electrophoresis confirmed the presence of the IgM together with albumin.

Affinity Chromatography Using Immobilized Sepharose-APA (Section 2 Step V)

Figure 4:
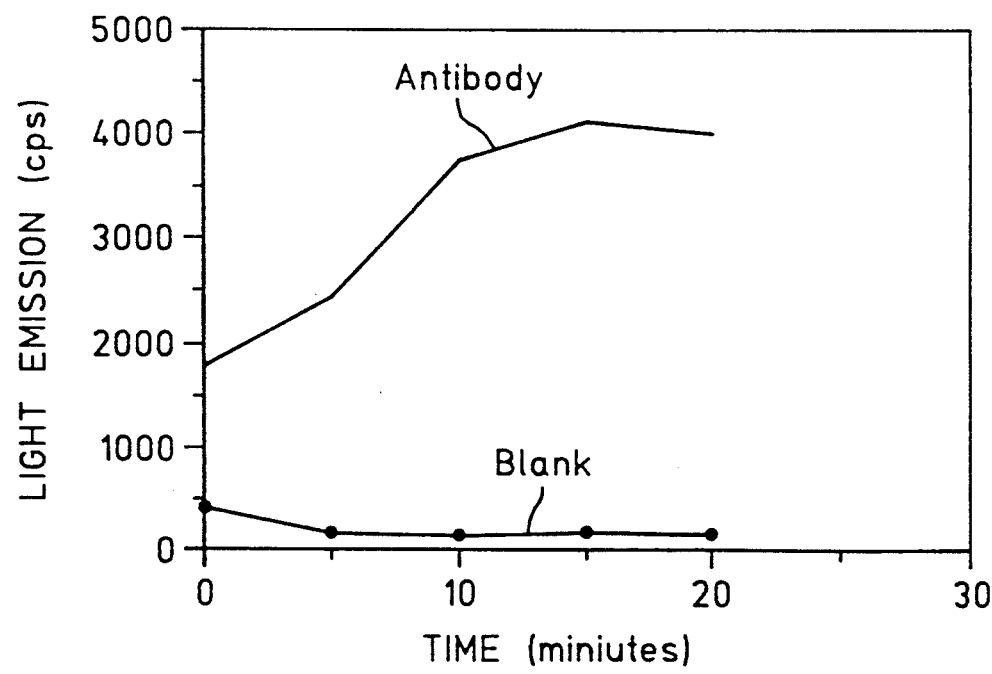

The antibody was purified using APA immobilized on Sepharose. In the batch purification an active material bound to the Sepharose-APA (FIG. 4). FIG. 4 shows the effect of the bound antibody in the chemiluminescent screening test.

Both the acidic and basic conditions eluted active material from the column. The kinetics of the reaction with the antibody were very slow and the greatest effect was seen after many hours of incubation. Agarose gel electrophoresis showed that a pure IgM fraction eluted from the column (acid and basic elution) and that the albumin and the band migrating in the fast gamma were not retained by the column.

Control Experiment: Testing of Irrelevant IgM Monoclonals (Section 2 Step VII)

No catalytic activity was found at any of the dilutions of the monoclonal IgM kappa and IgM lambda antibodies tested.

This Example has shown the preparation of a monoclonal antibody of use in increasing the light output from a chemiluminescent reaction. The monoclonal antibody isolated was identified as being of the IgM kappa class. Extensive purification steps were undertaken and the best results were obtained after affinity chromatography using immobilised Sepharose-APA. Using these techniques, monoclonal antibodies raised against other chemiluminescent reaction intermediates can be isolated. It is believed that monoclonals of the IgG class will further increase light output.

I claim:

1. A method of increasing the light output from a chemiluminescent reaction of a dihydrophthalazinedione (DPD) with an oxidant, said DPD being substituted in its benzene ring, which method comprises the step of carrying out said reaction in the presence of at least one antibody raised against the ground state of the emitting species of the chemiluminescent reaction which antibody increases the light output of said chemiluminescent reaction, said ground state being the phthalic acid which is substituted in its benzene ring in the same manner as the DPD.

2. A method according to claim 1, wherein the antibody is produced by a process comprising the steps of:
   (a) generating a plurality of antibodies to the ground state of the emitting species of said chemiluminescent reaction; and
   (b) screening said plurality of antibodies to identify at least one antibody that increases the light output of said chemiluminescent reaction.

3. A method according to claim 1, wherein said at least one antibody is a monoclonal antibody.

4. A method according to claim 3, wherein said at least one antibody is of the IgM or IgG class.

5. A method of increasing the light output from a chemiluminescent reaction of luminol with an oxidant, which method comprises the step of carrying out said reaction in the presence of at least one antibody raised against 3-aminophthalic acid which antibody increases the light output of said chemiluminescent reaction.

6. A method according to claim 1, wherein the antibody is free or conjugated to a ligand and the presence or amount of the antibody is determined from the presence or amount of light output.

7. A method according to claim 1, wherein the oxidant is hydrogen peroxide.

8. An antibody raised against the ground state of the emitting species of a chemiluminescent reaction of a dihydrophthalazinedione (DPD) with an oxidant, said DPD being substituted in its benzene ring which antibody increase the light output of said chemiluminescent reaction, said ground state being the phthalic acid which is substituted in its benzene ring in the same manner as the DPD.

9. An antibody raised against 3-aminophthalic acid.

10. A kit comprising in separate containers:
    a chemiluminescent dihydrophthalazinedione (DPD), said DPD being substituted in its benzene ring; and
    an antibody raised against the ground state of the emitting species of a chemiluminescent reaction of a dihydrophthalazinedione (DPD), said DPD being substituted in its benzene ring which antibody increase the light output of said chemiluminescent reaction, said ground state being the phthalic acid which is substituted in its benzene ring in the same manner as the DPD.

11. A kit according to claim 10, wherein the antibody is a monoclonal antibody.

12. A kit according to claim 10, wherein the antibody is conjugated to a ligand.

13. A kit according to claim 10, which further comprises an oxidant.

14. A kit according to claim 13, wherein the oxidant is hydrogen peroxide.

15. A kit comprising in separate containers:
    luminol; and
    an antibody raised against 3-aminophthalic acid.

* * * * *